United States Patent [19]

Fresco

[11] Patent Number: 5,422,251

[45] Date of Patent: Jun. 6, 1995

[54] TRIPLE-STRANDED NUCLEIC ACIDS

[75] Inventor: Jacques R. Fresco, Princeton, N.J.

[73] Assignee: Princeton University, Princeton, N.J.

[21] Appl. No.: 187,890

[22] Filed: Jan. 28, 1994

Related U.S. Application Data

[63] Continuation of Ser. No. 841,218, Feb. 27, 1992, which is a continuation of Ser. No. 622,330, Nov. 27, 1990, abandoned, which is a continuation of Ser. No. 366,244, Jun. 9, 1989, abandoned, which is a continuation of Ser. No. 935,047, Nov. 26, 1986, abandoned.

[51] Int. Cl.$^6$ .................. C12Q 1/68; C07H 21/04; C12P 19/34
[52] U.S. Cl. .................. 435/91.1; 536/24.31; 536/24.32; 435/6
[58] Field of Search ............... 435/6, 91.1; 536/24.31, 536/24.32

[56] References Cited

FOREIGN PATENT DOCUMENTS 0375408 6/1990 European Pat. Off. .

OTHER PUBLICATIONS

Letai et al. Biochemistry 27:9108–9112, 1988.
Cooney et al. Science 241: 456–459, 1988.
Broitmon et al. Proc. Natl. Acad. Sci. 84:5120–5124, 1987.
Poitel et al. Proc. Natl. Acad. Sci. 88:8227–8231, 1991.
Felsenfeld, G. et al., "Studies on the Formation of Two- and Three-Stranded Polyribonucleotides", *Biochimica Et Biophysica Acta*, vol. 26, (1957), pp. 457–468.
Fresco, J. et al., "Polynucleotides. I. Molecular Properties and Configurations of Polyribodenylic Acid in Solution", *J. Am. Chem. Soc.* vol. 79, (1957), pp. 3928–3929.
Rich, A., "A Hybrid Helix Containing Both Deoxyribose and Ribose Polynucleotides and Its Rel. to the Transfer of Info. Bet. the Nuc. Acids," *PNAS*, vol. 48, (1960), pp. 1044–1053.
Fresco, J., "The Accommodations of Noncomplementary Bases in Helical Polyribonucleotides and Deoxyribonucleic Acids", *Proc. Natl. Acad. Sci.*, vol. 46, No. 3, (1960) 311–321.
Schildkraut, C. et al., "Formation and Properties of Polyribunucleotide–Polydeoxyribonucleotide Helical Complexes", *The J. of Biological Chemistry*, vol. 236, No. 1, (1961), PC3–PC4.
Josse, J. et al., "Enzymatic Synthesis of Deoxyribonucleic Acid", *The Journal of Biological Chemistry*, vol. 236, No. 3, (1961), pp. 864–875.
Fresco, J., "Some Investigations of the Secondary and Tertiary Structure of Ribonucleic Acids", *Informational Macromolecules*, (1963), pp. 121–142.
Stevens, C. et al., "The Conversion of Two-Stranded Poly(A+U) to Three-Strand Poly (A+2U) and Poly A by Heat", *Biopolymers*, vol. 2, No. 4, (1964), pp. 293–314.
Lipsett, M., "Complex Formation Between Polycytidylic Acid and Guanine Oligonucleotides", *The Journal of Biological Chemistry*, vol. 239, No. 4, (1964), pp. 1256–1260.
Blake, R. et al., "Spectrophotometric Study of the Kinetics of Formation of the Two-Stranded Helical Complex Resulting From the Interaction of Polyriboadenylate and Polyribouridylate", *J. Mol. Biol.*, vol. 19, (1966), pp. 145–160.

(List continued on next page.)

*Primary Examiner*—Mindy B. Fleisher
*Attorney, Agent, or Firm*—Glenn E. Kara

[57] ABSTRACT

A triple-stranded nucleic acid having a first nucleic acid strand that has a region of adjacent purine nucleoside residues; a second nucleic acid strand, at least a portion of which is hydrogen bonded in a Watson-Crick manner to the region of adjacent purine nucleoside residues of the first strand; and a third nucleic acid strand, at least a portion of which is hydrogen bonded to the portion of the region of adjacent purine nucleoside residues of the first strand, the portion of the region of adjacent purine nucleoside residues to which both the second strand and the third strand are bonded defining the triple-stranded nucleic acid.

18 Claims, 12 Drawing Sheets

OTHER PUBLICATIONS

Riley, M., et al., "Physical and Chemical Characterization of Two- and Three Stranded Adenine-Uracil Homopolymer Complexes", *J. Mol. Biol.*, vol. 20, (1966), pp. 359-389.

Morgan, A. R. et al., "Specificity of the Three-Stranded Complex Formation Between Double-stranded DNA and Single-stranded RNA Containing Repeating Nucleotide Sequences". *J. Mol. Biol.* vol. 37, (1968), pp. 63-80.

Blake, R. et al., "Polynucleotides. IX. Temperature Dependence of a Kinetics of Complex Formation in Equimolar Mixtures of Polyriboadenylate and Polyribouridylate," *J. of the American Chemical Society*, vol. 90, (1968), pp. 3556-3562.

Lomant, A. et al., "Structural and Energetic Consequences of Noncomplementary Base Oppositions in Helices", *Prog. Nuc. Acid Res. & Mol. Biol.*, vol. 15, (1975), pp. 185-218.

Dolan, M. et al., "Analysis of the Adult Chicken $\beta$-Globin Gene", *The J. of Biological Chemistry*, vol. 258, No. 6, (1983), pp. 3983-3990.

Arnott, S., et al., "Models of Triple-Stranded Polynucleotides with Optimised Stereochemistry", *Nucleic Acids Research*, vol. 3, No. 10, (1976), pp. 2459-2470.

Thiele, D., et al., "Evidence For a Three Stranded Complex Between Poly I and Poly C", *FEBS Letters*, vol. 1, No. 3, (1968), pp. 173-175.

Pardee, A. B., et al., "On the nature of the repressor of $\beta$-galactosidase synthesis in *Escherichia coli*", *Bichimica et Biophysica Acta*, vol. 36, No. 2, (1959), pp. 545-547.

Blake, R. D., et al., "Polynucleotides. XI. Thermodynamics of $(A)_N \cdot 2(U)_\infty$. From the Dep. of $T_m N$ on Oligomer Length", *Biopolymers*, vol. 12, No. 4, (1973) pp. 775-789.

Hattori, M., et al., "The Structure of Triple-Stranded Go2C Polynucleotide Helices", *Biopolymers*, vol. 15, No. 3, (1976), pp. 523-531.

Howard, F. B., et al., "Interaction of Poly(A) and Poly(I)", *Biochemistry*, vol. 16, No. 21, (1977), pp. 4647-4650.

Blake, R. D., et al., "A Spectral Approach to the Equilibria between Polyriboadenylate and Polyribouridylate and their Complexes", *J. of Mol. Biol.*, vol. 30, (1967), pp. 291-308.

Howard, F. B., et al., "Interaction of Polyribothymidylic Acid with Polyadenylic Acid", *The Journal of Biological Chemistry*, (1971), vol. 246, No. 23, pp. 7073-7086.

Felsenfeld, G., "Theoretical Studies on the Interaction of Synthetic Polyribonucleotides", *Biochimica et Biophysica Acta*, vol. 29, No. 29, (1958), pp. 133-144.

Arnott, S., et al., "Structures for Poly(U)·poly(A)·poly(U) Triple Stranded Polynucleotides," *Nature New Biology*, vol. 244, (1973), pp. 99-101.

FIG. 1

| Strand number[b] | 3 1 2<br>↑ ↑[a] | 3 1 2<br>↑ ↑ | 3 1 2<br>↑ ↑ | 3 1 2<br>↑ ↑ |
|---|---|---|---|---|
| | A•A•T | G•G•C | G•G•C | C•G•C |
| | G•G•C | G•G•C | T•A•U | U•A•U |
| | C•G•C | G•G•C | T•A•U | U•A•U |
| | T•A•T | U•A•T | C•G•C | A•A•U |
| | T•A•T | U•A•T | T•A•U | G•G•C |
| | C•G•C | C•G•C | G•G•C | U•A•U |
| | A•A•T | G•G•C | C•G•C | U•A•U |
| | C•G•C | C•G•C | C•G•C | A•A•U |
| | A•A•T | A•A•T | C•G•C | U•G•C |
| | A•A•T | A•A•T | A•A•U | G•G•C |
| | G•G•C<br>↓<br>d d d[c] | U•A•T | ↓<br>d r r[d] | ↓<br>r r r |
| | | G•G•C<br>↓<br>r d d | | |

[a] The arrows represent strand orientation. In all four structures strand 3 is parallel to strand 1, and strand 2 is anti-parallel to strand 1.

[b] All four structures are in the A conformation.

[c] d = DNA strand.

[d] r = RNA strand.

TRIPLE-STRANDED NUCLEIC ACIDS

This is a continuation of application Ser. No. 07/841,218 filed Feb. 27, 1992, which is a continuation of application Ser. No. 07/622,330 filed Nov. 27, 1990, now abandoned, which was a continuation of application Ser. No. 07/366,244 filed Jun. 9, 1989, now abandoned, which was a continuation of application Ser. No. 06/935,047 filed Nov. 26, 1986, now abandoned.

BACKGROUND OF THE INVENTION

This invention relates to triple-stranded nucleic acids.

Such nucleic acids have been observed in which a central polyadenylate (poly(A)) strand is hydrogen bonded to two polyridylate (poly(U)) strands (e.g., Felsenfeld et al., 26 Biochim. Biophys. Acta. 457 (1957)). This triple-stranded structure has been described by Arnott et al., 244 Nature New Bio. 99 (1973), as having one poly(U) strand hydrogen bonded to the poly(A) strand in the Watson-Crick manner, and the second poly(U) strand hydrogen bonded to the poly(A) strand in a Hoogsteen-type arrangement, with the second poly(U) chain being oriented parallel to the poly(A) strand. Watson-Crick manner, as used herein, means the standard hydrogen bonding arrangement that is present in double-stranded nucleic acids (A·T/U, G·C).

Howard et al., 246 J. Biol. Chem. 7033 (1971), describe a triple-stranded nucleic acid having a central polydeoxyadenylate (poly(dA)) strand hydrogen bonded to two polydeoxythymidylate (poly(dT)) strands. Arnott et al., 3 Nuc. Acid Res. 2459 (1976), say that both this structure and poly(U)·poly(A)·poly(U) exist as A-type helices.

Other triple-stranded nucleic acids that have been reported include a central polyguanylate (poly(G)) strand hydrogen bonded to two polycytidylate (poly(C)) strands (Lipsett, 239 J. Biol. Chem. 1256 (1964)); a central poly(G) strand hydrogen bonded to a poly(C) strand and a second poly(G) strand (Fresco, in Informational Macromolecules: A Symposium. 121 (1963)); a central polyinosinate (poly(I)) strand hydrogen bonded to two poly(C) strands (Arnott et al., 3 Nuc. Acid Res. 2459 (1976)); and a-central poly(dA-dG) strand (in which deoxyadenosine and deoxyguanosine residues alternate) hydrogen bonded to a poly(dT-dC)-strand (in which deoxythymidine and deoxycytidine residues alternate) and a poly(U-C) strand (in which uridine and cytidine residues alternate) (Morgan et al., 37 J. Mol. Bio. 63 (1968)).

SUMMARY OF THE INVENTION

The invention concerns a triple-stranded nucleic acid having a first nucleic acid strand that has a region of adjacent purine nucleoside residues; a second nucleic acid strand, at least a portion of which is hydrogen bonded in a Watson-Crick manner to the region of adjacent purine nucleoside residues of the first strand; and a third nucleic acid strand, at least a portion of which is hydrogen bonded to the portion of the region of adjacent purine nucleoside residues of the first strand, the portion of the region of adjacent purine nucleoside residues to which both the second strand and the third strand are bonded defining the triple-stranded nucleic acid.

In one aspect, the invention features such a nucleic acid in which the portion of the third strand hydrogen bonded to the region of adjacent purine nucleoside residues includes both purine and pyrimidine nucleoside residues.

In another aspect, the invention features such a triple-stranded nucleic acid in which the portion of the third strand hydrogen bonded to the region of adjacent purine nucleoside residues includes at least one adenosine residue.

In another aspect, the invention features such a triple-stranded nucleic acid in which the portion of the region of adjacent purine nucleoside residues hydrogen bonded to both the second and the third strand includes both guanosine and adenosine residues in a manner whereby they do not alternate along the entire length of the portion of adjacent purine nucleoside residues.

In preferred embodiments, all of the purine nucleoside residues in the portion of the third strand hydrogen bonded to the region of adjacent purine nucleoside residues are adenosines, guanosines, or a mixture of adenosines and guanosines. In other preferred embodiments, each adenosine in the region of adjacent purine nucleoside residues that is hydrogen bonded to a portion of the third strand is hydrogen bonded to either inosine, uridine, thymidine, or adenosine in the portion, and each guanosine in the region of adjacent purine nucleoside residues that is hydrogen bonded to a portion of the third strand is hydrogen bonded to either inosine, cytidine, or guanosine in the portion.

In other preferred embodiments, the third strand is oriented parallel to the first strand; the first and second strands are RNA or DNA; the third strand is RNA or DNA; and the region of adjacent purine nucleoside residues is at least 10 nucleoside residues in length.

In another aspect, the invention features a method of forming a triple-stranded nucleic acid, the method including the steps of providing a first nucleic acid strand that includes a region of adjacent purine nucleoside residues; providing a second nucleic acid strand at least a portion of which is hydrogen bonded in a Watson-Crick manner to the region of adjacent purine nucleoside residues; providing a third nucleic acid strand at least a portion of which is correspondent to a portion of the region of adjacent purine nucleoside residues of the first strand, wherein the portion of the third strand includes at least one guanosine, cytidine, or inosine residue; and contacting the first and second strands with the third strand at a pH between 6 and 8 under ionic conditions which allow formation of stable bonds between the guanosine, cytidine, or inosine residue in the third-strand and a corresponding residue in the region of adjacent purine nucleoside residues to allow the portion of the third strand to hydrogen bond to the region of adjacent purine nucleoside residues to yield the triple-stranded nucleic acid; wherein the portion of the region of adjacent purine nucleoside residues to which both the second strand and the third strand are bonded defines the triple-stranded nucleic acid.

In preferred embodiments the residue in the third strand, in order to hydrogen bond to its bonding partner (i.e., correspondent) in the region of adjacent purine nucleoside residues, undergoes protonation that is energetically unfavorable at pH 6–8, and the ionic conditions reduce the electrostatic potential of phosphate groups in the third strand to compensate energetically for the unfavorable protonetion. In other embodiments, ionic conditions are the presence of cations such as $Mg^{+2}$, $Mn^{+2}$, and $Ca^{+2}$ that site bind to charged phosphate groups of the third nucleic strands to neutralize the charges, or the presence of cations such as Na+, Li+, K+, or tetramethylammonium that shield the charged phosphate groups. In other embodiments, the corresponding bonding partner in the region of adjacent purine nucleoside residues is guanosine.

In order to hydrogen bond to a region of adjacent purines in the first strand, a third strand must have an appropriately corresponding sequence, i.e., each residue in the region of adjacent purines has a correspondent hydrogen bonding partner in the third strand. The following matrix shows the correspondent pairing that is present in the preferred embodiments (+ means the bases are correspondent; − means the bases are not correspondent):

|  | Third-strand Residues | | | | |
| --- | --- | --- | --- | --- | --- |
|  | A | U/T | I | G | C |
| Watson-Crick Core Polypurine Strand Residues | | | | | |
| A | + | + | + | − | − |
| G | − | − | + | + | + |

The terms correspondent and corresponding, as used herein, are used to differentiate third-strand hydrogen bonding from standard Watson-Crick hydrogen bonding, in which the terms complement and complementary are commonly used to describe A·T, A·U, and G·C pairing.

The recognition that segments of adjacent purine nucleoside residues (in double-stranded nucleic acids) containing any (random) sequence of adenosine and guanosine residues can serve as targets for third strand nucleic acid binding, and the determination of which bases in the third strand can hydrogen bond to which purine residue correspondent, makes possible a new type of assay in which denaturation of double-stranded nucleic acids containing a target sequence is unneccessary. The recognition of the fact that, of the natural nucleic acid residues, third strand adenosine, uridine, and thymidine residues will hydrogen bond only to an adenosine residue in a target region (of adjacent purine nucleoside residues); and that third strand guanosine and cytidine residues will hydrogen bond only to a guanosine residue in a target region (of adjacent purine nucleoside residues), allows for selection of probe sequences that are specific for any distinctive all-purine residue sequence contained in the double-stranded nucleic acid of a target organism. Moreover, the recognition of the fact that such triple-stranded structures can form under physiological conditions (i.e., those conditions found inside a cell) opens up the possibility of controlling gene-expression by formation of triple-stranded structures inside a cell.

Other features and advantages of the invention will be apparent from the following description of the preferred embodiments and from the claims.

DESCRIPTION OF THE PREFERRED EMBODIMENTS

I now describe the structure and use of the preferred embodiments, after first briefly describing the drawings.

DRAWINGS

FIG. 1 is a diagrammatic illustration of examples of triple-stranded nucleic acid structures.

STRUCTURE

The triple-stranded nucleic acids of the invention can form where one strand of a standard Watson-Crick double helix has a region of generally at least 10 adjacent purine nucleoside residues (polypurine segment). A third strand can hydrogen bond to the polypurine segment because purine members of Watson-Crick pairs have two remaining hydrogen bond donor or acceptor sites available to further hydrogen bond to correspondent purine or pyrimidine residues in the third strand. An adenosine residue in the polypurine segment can hydrogen bond to either an adenosine, uridine, thymidine, or inosine residue in the third strand. A guanosine residue in the polypurine region can hydrogen bond to either a guanosine, inosine, or cytidine residue in the third strand. A third strand can hydrogen bond to the polypurine region to form a triple-stranded nucleic acid if each residue in the polypurine segment has a corresponding hydrogen bonding partner in the third strand and is of the same 5' to 3' orientation or polarity as the polypurine strand (i.e., is parallel to that strand). Examples of triple-stranded structures that can form are shown in FIG. 1.

A polypurine segment in one strand of a double-stranded DNA can hydrogen bond to either a RNA or a DNA strand that has a corresponding residue alignment. Similarly a polypurine segment in one strand of a double-stranded RNA can hydrogen bond to either a RNA or a DNA strand that has a corresponding residue alignment. Likewise, should a double-stranded nucleic acid have one RNA and one DNA strand, and one of those strands has a polypurine segment, that segment can hydrogen bond to either a corresponding DNA or a corresponding RNA strand segment of the correct polarity.

Figure 2A:
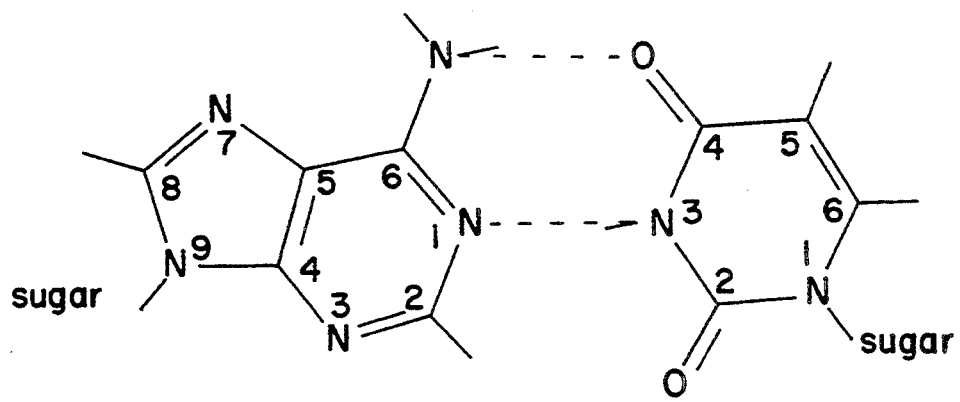
FIG. 2(a) is a diagrammatic illustration of the hydrogen bonding that is present in the adenine-uracil base pair.
Figure 2B:
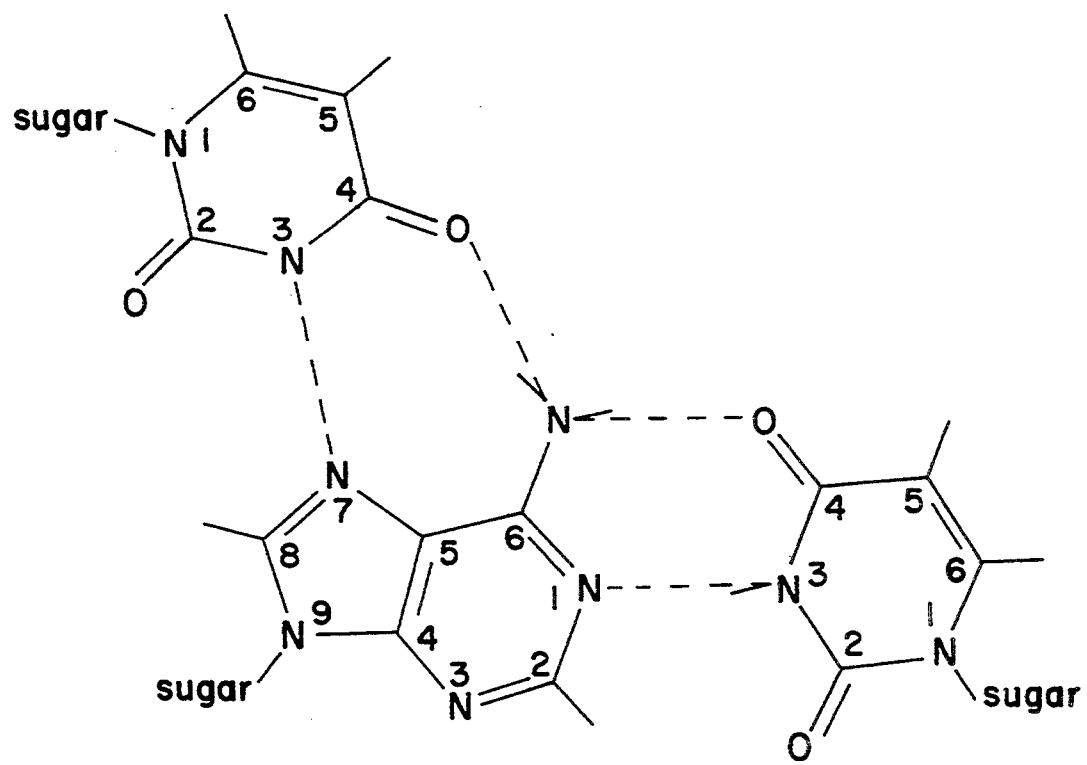
FIG. 2(b) is a diagrammatic illustration of the hydrogen bonding that may be present in the base triplet uracil-adenine-uracil/thymine.

FIG. 2 shows the hydrogen bonding that may be present in the base triplet uracil-adenine-uracil (U·A·U). FIG. 2a illustrates the hydrogen bonding that occurs between adenine and uracil in a double-stranded nucleic acid structure. $N_1$ of adenine is hydrogen bonded to $N_3$ of uracil, and $C_6$-N of adenine is hydrogen bonded to $C_4=O$ of uracil. FIG. 2b illustrates the possible hydrogen bonding of adenine in the double-stranded structure of FIG. 2a and a uracil in the third strand. The remaining $C_6$-N proton and $N_7$ of the adenine are hydrogen bonded, respectfully, to $N_3$ and $C_4=O$ of the second uracil. The triplets thymine-adenine-uracil (T·A·U), thymine-adenine-thymine (T·A·T), and uracil-adenine-thymine (U·A·T) can have hydrogen bonding patterns analogous to that for U·A·U.

Figure 3A:
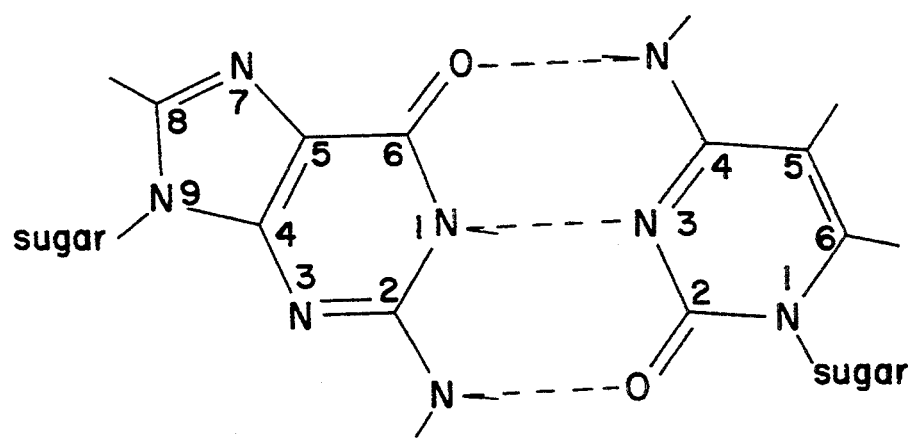
FIG. 3(a) is a diagrammatic illustration of the hydrogen bonding that is present in the guanine-cytosine base pair.
Figure 3B:
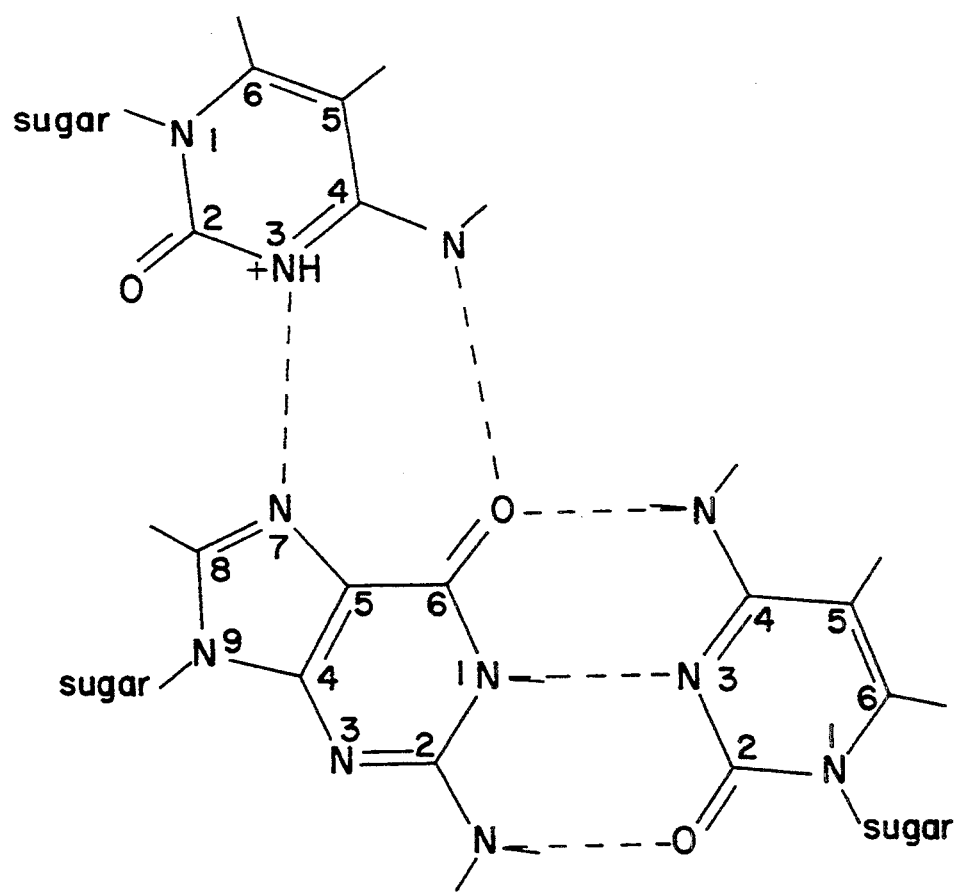
FIG. 3(b) is a diagrammatic illustration of the hydrogen bonding that may be present in the base triplet cytosine-guanine-cytosine.

FIG. 3 shows the presumed hydrogen bonding in the base triplet cytosine-guanine-cytosine (C·G·C). FIG. 3a illustrates the hydrogen bonding of cytosine and guanine in a standard double-stranded nucleic acid structure. $N_1$, $C_2$-N, and $C_6=O$ of guanine are hydrogen bonded, respectively, to $N_3$, $C_2=O$, and $C_4$-N of cytosine. FIG. 3b illustrates the bonding that can occur between the guanine of FIG. 3a and a cytosine in the third strand. That (second) cytosine must be protonated at $N_3$ for hydrogen bonding to occur with $N_7$ of guanine; $C_4$-N of the second cytosine is also hydrogen bonded to the $C_6=O$ of the guanine. This structure is analogous, or isosteric, with that of the U·A·U triplet.

Figure 4:
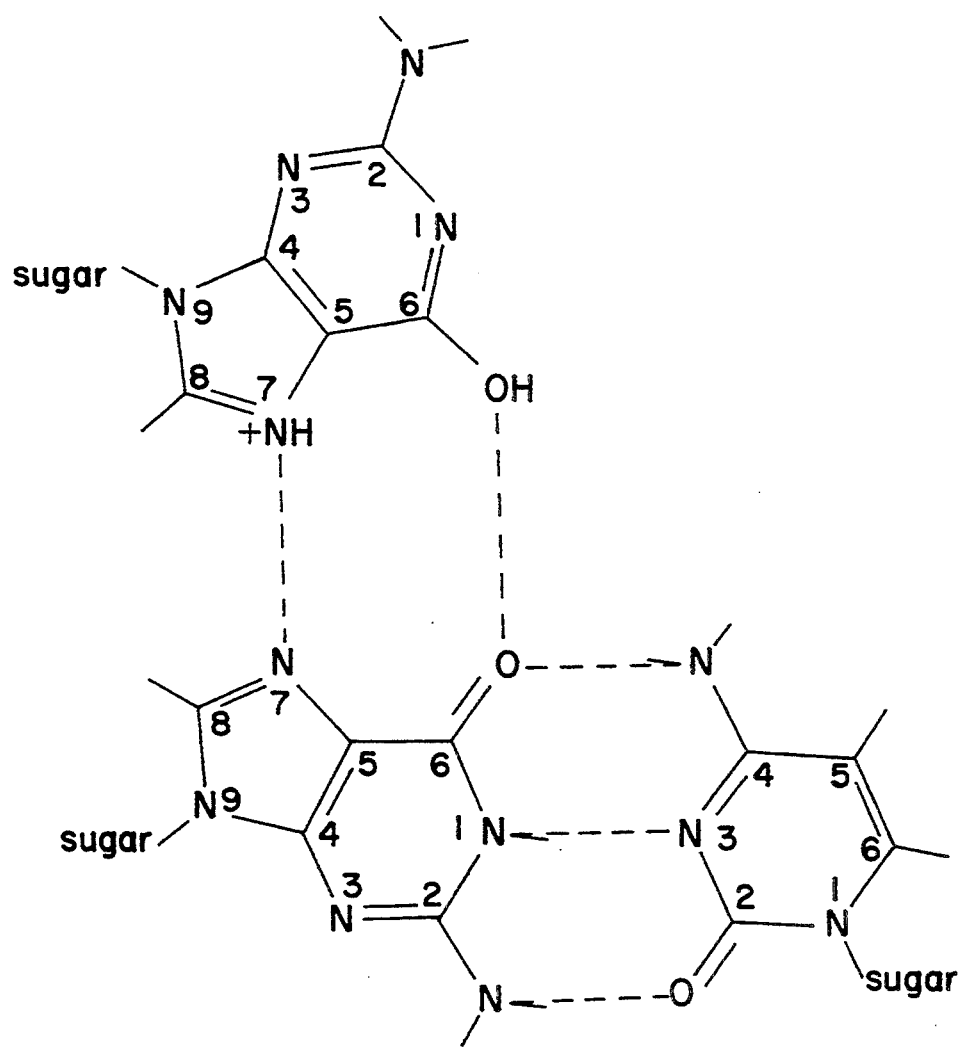
FIG. 4 is a diagrammatic illustration of the hydrogen bonding that may be present in the base triplet guanine-guanine-cytosine.

FIG. 4 shows the hydrogen bonding that may be present in the base triplet guanine-guanine-cytosine (G·G·C). The hydrogen bonding between cytosine and guanine in a double-stranded structure was illustrated in FIG. 3a. The guanine in the FIG. 3a structure can bond to a second guanine to form the triplet. For triplet formation, the second guanine must undergo changes: $N_7$ should be protonated, $C_6=O$ should tautomerize to $C_6$—OH, and the base must isomerize about the glycosyl bond from the anti to the syn orientation. The third requirement applies to all purine nucleoside residues in a third strand that contains both purines and pyrimidines. The syn configuration ensures that the glycosyl bond separation distance between the polypurine backbone C; and the third strand backbone C; is the same whether the third strand base is a purine or a pyrimidine; this allows for a regular winding of the third strand backbone about the double helix core. If the third strand contains all purine residues, the configuration about the glycosyl bonds of the residues can be either all syn or all anti in order to ensure consistent glycosyl bond separation. As shown in FIG. 4, $C_6=O$ and $N_7$ of the central (double-strand) guanine are hydrogen bonded respectively, to $C_6$—OH and $N_7$ of the third strand guanine. The triplet hypoxanthine-guanine-cytosine (I·G·C) can have a hydrogen bonding pattern similar to that in the triplet G·G·C.

Figure 5:
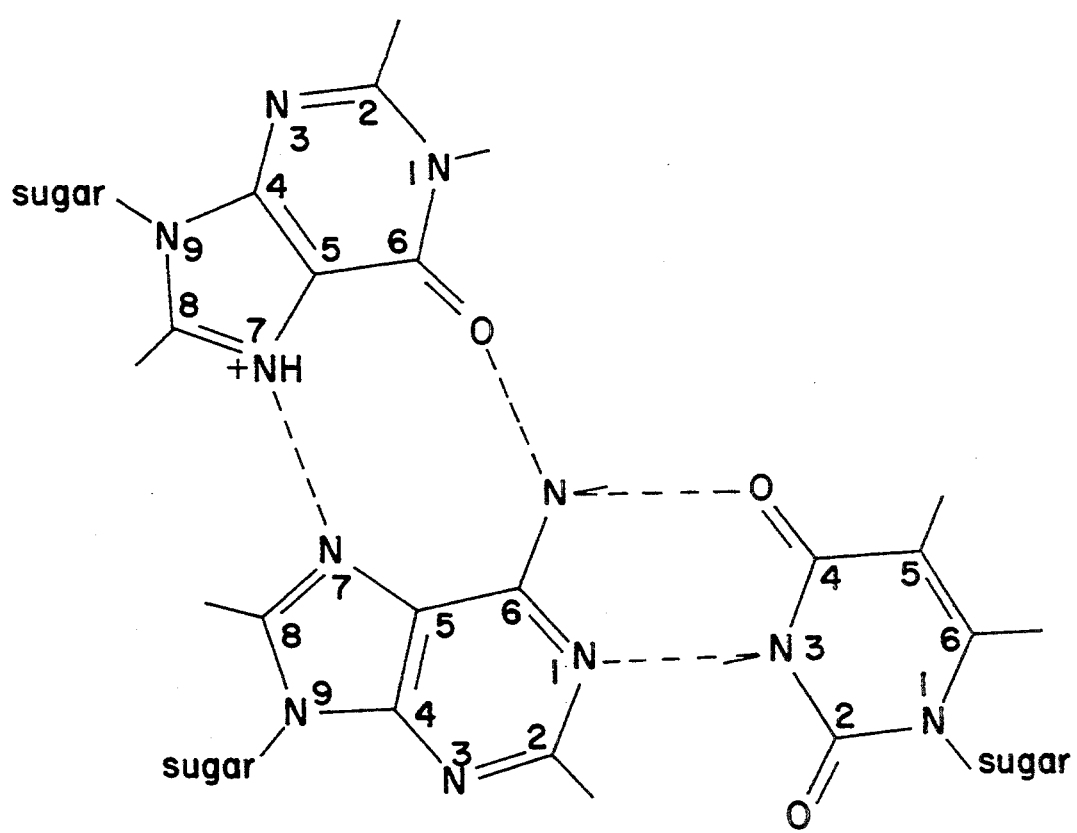
FIG. 5 is a diagrammatic illustration of the hydrogen bonding that may be present in the base triplet hypoxanthine-adenine-uracil/thymine.

FIG. 5 shows the hydrogen bonding that may be present in the triplet hypoxanthine-adenine-uracil (I·A·U). The hydrogen bonding between adenine and uracil in a double-stranded structure was illustrated in FIG. 2a. The adenine in FIG. 2a also can additionally bond to hypoxanthine to form a triplet. For triplet formation to occur, $N_7$ of hypoxanthine should be protonated, and hypoxanthine should be oriented syn about its glycosyl bond (assuming that the third strand hydrogen bonding segment of which hypoxanthine is a part contains a mixture of purines and pyrimidines). As shown in FIG. 5, $C_6=O$ and $N_7$ of hypoxanthine can hydrogen bond, respectively, to $C_6N$ and $N_7$ of adenine. In FIG. 5, uracil can be replaced by thymine, which can hydrogen bond to adenine in the same manner as uracil.

Figure 6:
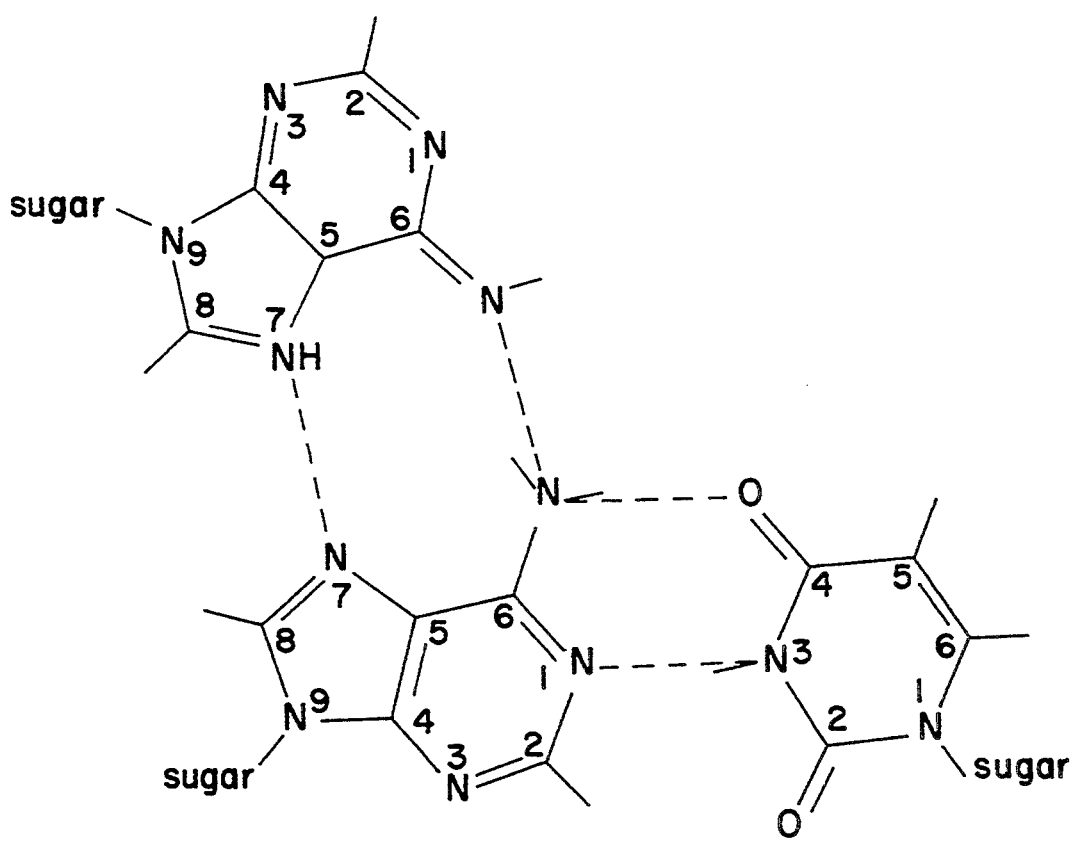
FIG. 6 is a diagrammatic illustration of the hydrogen bonding that may be present in the base triplet adenine-adenine-uracil/thymine.

FIG. 6 shows the hydrogen bonding that may be present in the triplet adenine-adenine-uracil (A·A·U). The hydrogen bonding between adenine and uracil in a double-stranded structure was illustrated in FIG. 2a. The adenine in FIG. 2a can also bond to a second adenine to form a triplet. For triplet formation to occur, $C_6$—N of the third strand adenine should exist in the imino tautomeric form, with a tautomeric shift occurring such that $N_7$ is protonated; and the third strand adenine should be oriented syn about its glycosyl bond (assuming that the third strand of which adenine is a part contains a mixture of purine and pyrimidine nucleoside residues). As shown in FIG. 6, $C_6=N$ and $N_7$ of the third strand adenine can hydrogen bond, respectively, to $C_6$—N and $N_7$ of the central adenine. In FIG. 6, uracil can be replaced by thymine which can bond to adenine in the same manner as uracil.

The third nucleic acid strand (that which hydrogen bonds to the double-stranded nucleic acid) is oriented parallel to the strand containing the polypurine segment and is wrapped around the double helix.

Triple-stranded nucleic acids exist in the A-type helix conformation. Third-strand binding to a DNA double helix, which in solution exists in the B conformation, requires the double helix to undergo a B→A conformational change. An RNA double helix, which already exists in the A conformation, requires no such conformational change. Two factors seem to make the A conformation preferable for triple helices. One is that the A conformation has a much larger major groove that can readily accommodate the third strand, something a B-DNA double helix cannot do. The second factor is that in B-DNA, the backbone phosphates are more or less symmetrically disposed about the helix axis. In contrast, in the A double helix, the two backbone strands are displaced away from the helix axis, which allows more favorable (symmetrical) distribution of the charges of the three backbone phosphates when the third strand is introduced.

The stability of third-strand binding is largely based on two factors: primarily on the energy derived from base stacking, which produces stabilizing $\pi$ orbital overlap between adjacent bases in the third strand, and secondarily on the hydrogen bonds between each base in the third strand and its purine correspondents in the polypurine segment of the double-helix. It is well known that in aqueous solution most of the energy for holding together the strands of a nucleic acid double helix is due to the interaction of the overlapping $\pi$ electrons of the bases and the tendency of the hydrophobic bases to minimize their interaction with the solvent; the hydrogen bonding between bases of the two strands contributes relatively little to the stability because of the high concentration of water molecules, which are both hydrogen donors and hydrogen acceptors and therefore are strong competitors of the hydrogen donors and acceptors of the bases. In general, stacked purines provide more effective $\pi$ electron overlap than stacked pyrimidines, especially where a large fraction of the stacked pyrimidines are uracil or thymine. In general, then, the larger the fraction of purine residues in the third strand, the better the $\pi$ electron overlap between stacked bases is likely to be, and the more stable the three stranded structure should be.

Generally, triple-stranded nucleic acids whose third strand and corresponding polypurine segment give rise to various combinations of base triplets described above can be formed up to 40° C. in the pH range of approximately 5 to 8 under appropriate ionic conditions, preferably the presence of some combination of site bound (e.g., $Mg^{+2}$, $Ca^{+2}$, or $Mn^{+2}$) and charge shielding (e.g., $Na^+$, $K^+$, or tetramethylammonium$^+$) cations.

Two general considerations determine the pH stability of triple-stranded nucleic acids: the effect of pH on the two strands that are hydrogen bonded in the standard Watson-Crick manner, and the effect of pH on third strand hydrogen bonding. In the physiological temperature range (0° C.–40° C.), Watson-Crick double-stranded nucleic acid helices are generally stable between pH 4 and 9, with some variation due to base composition (as is well known to those skilled in the art) and the ionic composition of the medium. In the same temperature range, stable third-strand hydrogen bonding to its corresponding polypurine segment can occur under comparable ionic condition over the narrower pH range of 5 to 8. Above pH 8, deprotonation of third strand guanosine, uridine, thymidine, and inosine residues begins to occur, which can detabilize third strand binding to double helices. Below pH 6, third strand guanosine, cytidine, and inosine residues protonate more readily, conferring added stability to triple helices with these residues. Below pH 5, however, protonation of third-strand adenosine residues begins to occur, which can destabilize the binding of third strands with adenosine residue sequences.

In the absence of appropriate or sufficient cation, the third-strand bases guanine, cytosine, and hypoxanthine do not protonate readily above pH 6, which weakens their binding to guanine bases of the purine segment of a double helix. This difficulty can be overcome if sufficient concentration of either site bound or charge shielding cations is present. Apparently, the cations effectively neutralize the phosphate charges of the third strand and so reduce their electrostatic potential, which results in third-strand binding being much more energetically favorable by compensating for the "cost" of protonation of third strand bases above their intrinsic pK's. Site bound cations (which generally are multivalent) bind directly to the phosphates and are very effective charge neutralizers. Charge shielding cations (which generally are monovalent) function via Debye-Huckel shielding and are two to three orders of magnitude less effective than site bound cations at neutralizing phosphate charges.

The concentration of cations that is necessary to stabilize triple-stranded nucleic acids that have guanosine, cytidine, or inosine residues in their third strands over the physiological temperature range varies with pH and the base composition of the third strand. The effect of pH has been discussed previously; accordingly, as the pH is lowered towards 6, a lower concentration of multivalent cation is needed in the presence of physiological saline (0.15 M NaCl), and below pH 6, stable triple-stranded nucleic acids can form without multivalent cation assistance. The same principles apply when only charge shielding cations are present. In addition, the larger the fraction of guanosine, cytidine, and inosine residues in the third strand, the higher the concentration of cation required to form stable triple-stranded structures above pH 6. At neutral pH, at least 1 mM (preferably at least 3 mM) of (unbound) site bound cations (e.g., $Mg^{+2}$), or at least 0.5 M (preferably 1 M) of charge shielding cations (e.g., $Na^+$) in all situations is generally sufficient to yield stable triple-stranded structures. It is noteworthy that the pH and ionic conditions favorable to third-strand binding mimic those found in the cell, i.e., approximately 5 mM $Mg^{+2}$ and 0.15 M $Na^+$.

A triple-stranded nucleic acid can be formed in an aqueous environment of suitable pH and ionic strength by interaction of a double-stranded nucleic acid having a polypurine segment and a third strand with a corresponding sequence to the polypurine sequence; the third strand binds to the polypurine segment in the parallel orientation to form the triple-stranded structure. The same triple-stranded nucleic acid structure also can be formed by mixing, in a proper aqueous environment, three nucleic acid strands, two of which are complementary in the standard Watson-Crick manner (and which bind to form a double helix), and the third strand being correspondent (as described above) to the sequence of the polypurine segment of one of the other two strands; the third strand will bind only if its sequence is correspondent to the polypurine segment in the parallel orientation.

Standard mixing curve experiments have been performed to determine the stoichiometry and specificity of third strand binding (i.e., which triplets can form). In one type of experiment, various combinations of pairs of homopolyribonucleotide chains were titrated. In the other type, homopolyribonucleotides were titrated with random copolynucleotiaes of determined composition that contain as their residues both the Watson-Crick complement to the homopolymer residues and a non-complementary Watson-Crick residue. In different experiments, the core double helix "host" Watson-Crick pairs in these combinations were either A·U or G·C. Copolymers were selected so as to test third-strand binding of various bases to the purine component of each of the Watson-Crick pairs.

The endpoints in such titration experiments are indicated by abrupt discontinuities in the changing ultraviolet absorbance with changing ratio of the interacting strands as the titration proceeds. Careful determination of endpoints corresponding to formation of triple-stranded helices, and analysis of the stoichiometry of strand interaction at those endpoints has allowed identification of third-strand residues that are hydrogen bonded to adenosine or guanosine residues of polypurine regions of Watson-Crick helices. Such determination and analysis of mixing curves are well known to those skilled in the art. Examples of such titrations are given below.

EXAMPLE 1

Figure 7:
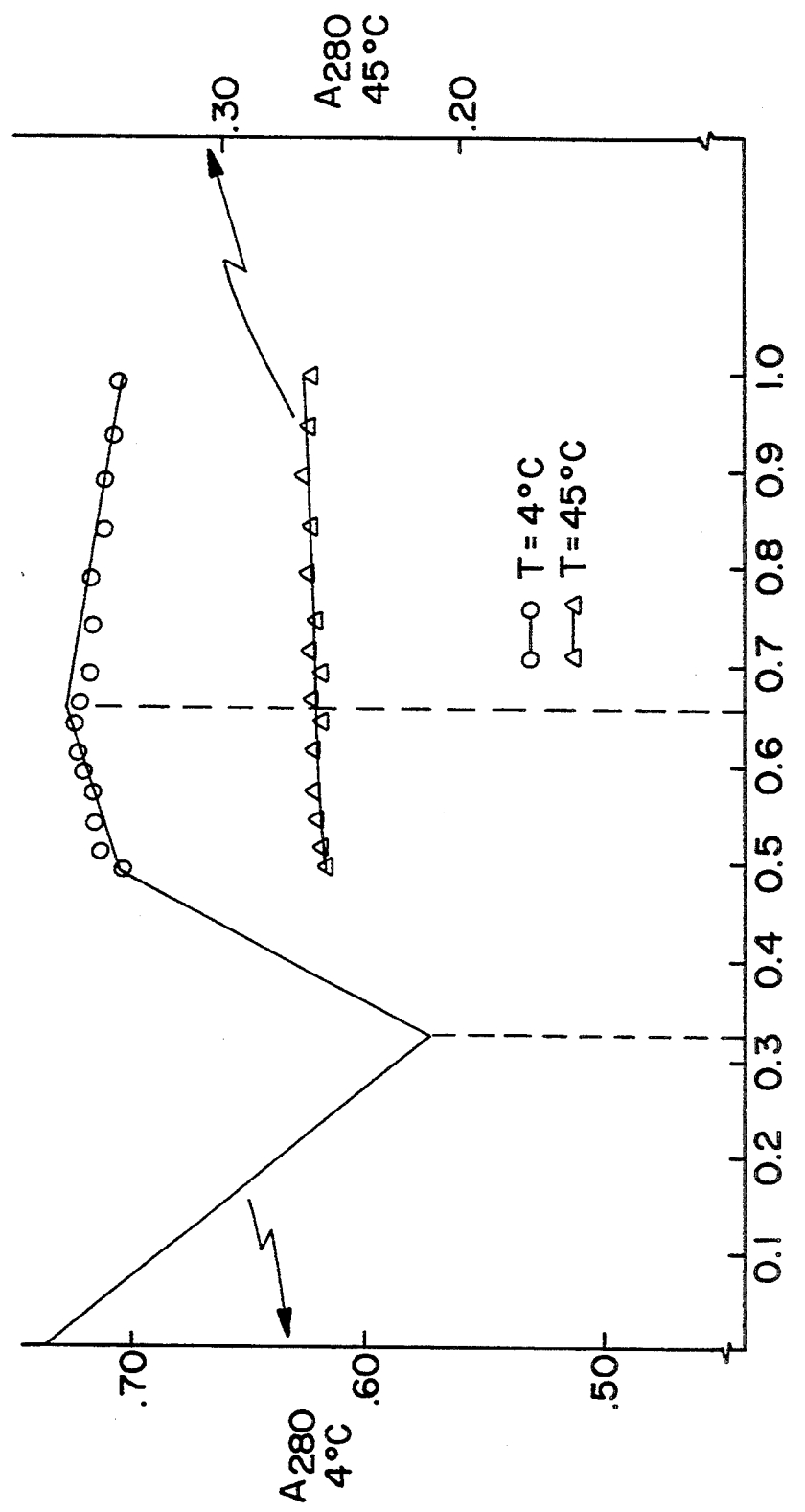
FIG. 7 is a mixing curve plot for the titration of poly(A) and poly(U).

FIG. 7 shows a mixing curve plot for the titration of poly(A) and poly(U) at 4° C., pH 7, in the presence of 5 mM $Mg^{+2}$ and 0.15 M $Na^+$. The plot contains three endpoints, of which two, corresponding to the formation of poly (A·U) ($X_A=0.5$) and poly (U·A·U) ($X_A=0.33$), were previously recognized from work in non-physiological solvents (e.g., Felsenfeld et al., 26 Biochem. Biophys. Acta 457 (1983); Blake et al., 30 J. Mol. Biol. 291 (1967)). The new endpoint, at $X_A=0.67$, corresponds to a helix containing the triplet A·A·U.

EXAMPLE 2

Figure 8:
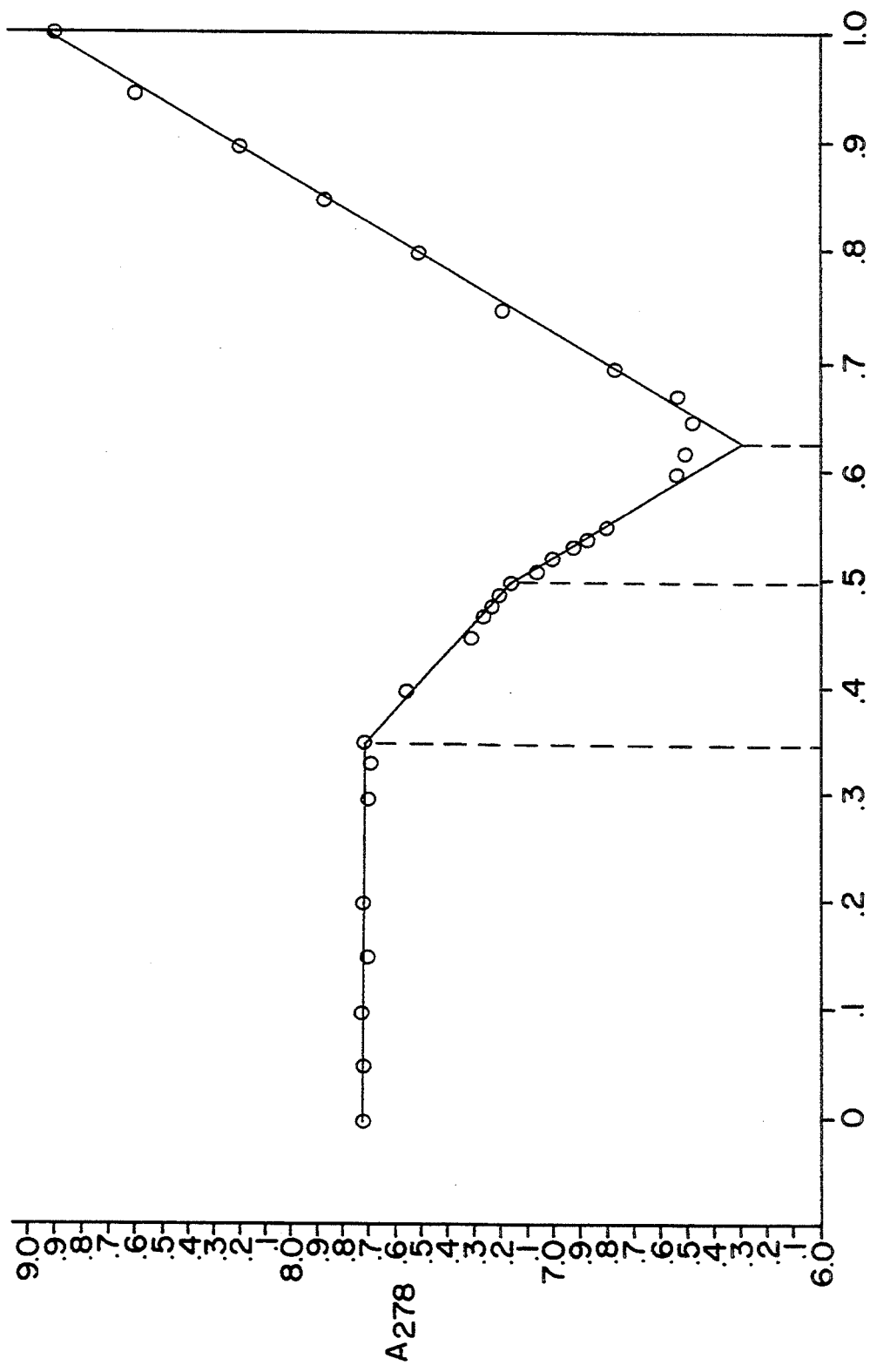
FIG. 8 is a mixing curve plot for the titration of poly-($A_{86}$, $I_{14}$) and poly(U).

FIG. 8 shows the mixing curve plot for the titration of poly($A_{86}$, $I_{14}$) (where the subscripts are the mole fractions of the residues in the random sequence copolymer) and poly(U). The titration was performed at 4° C. and neutral pH in the presence of 5 mM $Mg^{+2}$ and 0.15 M $Na^+$. The endpoint at $X_u=0.33$ corresponds to a complex containing the triplets A·A·U, I·A·U, (and A·I·U). The endpoint at $X_u=0.67$ corresponds to a complex containing the triplets U·A·U (and U·I·U).

EXAMPLE 3

Figure 9:
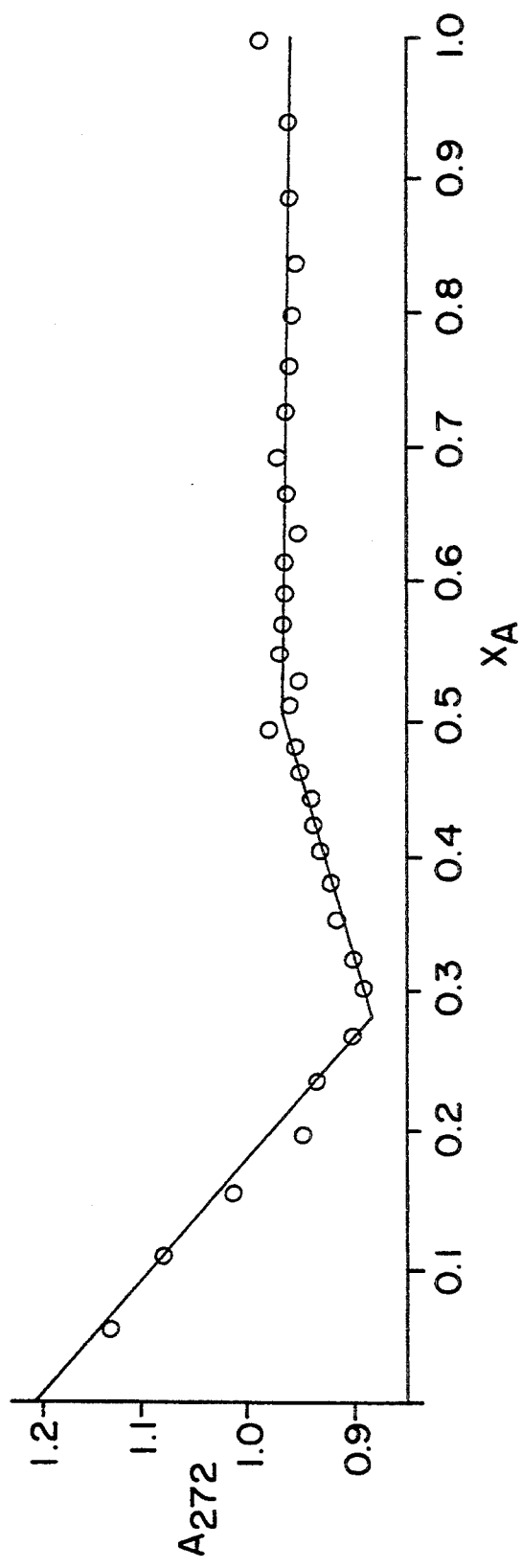
FIG. 9 is a the mixing curve plot for the titration of poly(A) and poly($U_{80}$, $C_{20}$).

FIG. 9 shows the mixing curve plot for the titration of poly(A) and poly($U_{80}$, $G_{20}$) at 4° C., pH 6.8, in the presence of 5 mM $Mg^{+2}$ and 0.15 M $Na^+$. The endpoint at $X_A=0.28$ is consistent with third strand U residues, but not third strand G residues being hydrogen bonded to the poly(A) strand of the core helix. Hence, the potential G·A·U triplet did not form.

EXAMPLE 4

Figure 10:
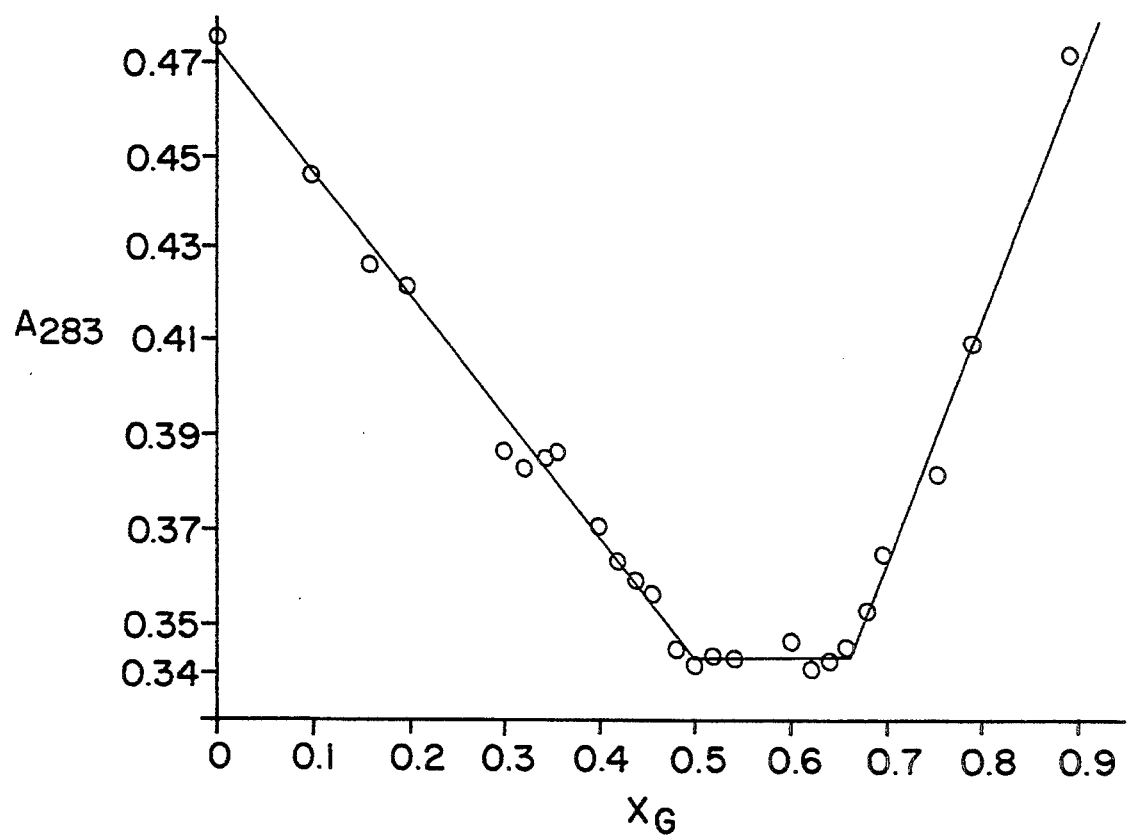
FIG. 10 is a mixing curve plot for the titration of poly(G) and poly($C_{88}$, $8BrA_{12}$).

FIG. 10 shows the mixing curve plot for titration of poly(G) and poly($C_{88}$, $8BrA_{12}$) at 20° C., pH 7, in the presence of 5 mM $Mg^{+2}$ and 0.15 M $Na^+$. The endpoint at $X_G=0.67$ corresponds to a three stranded complex containing the triplets G·G·C (and G·G·8BrA).

EXAMPLE 5

Figure 11:
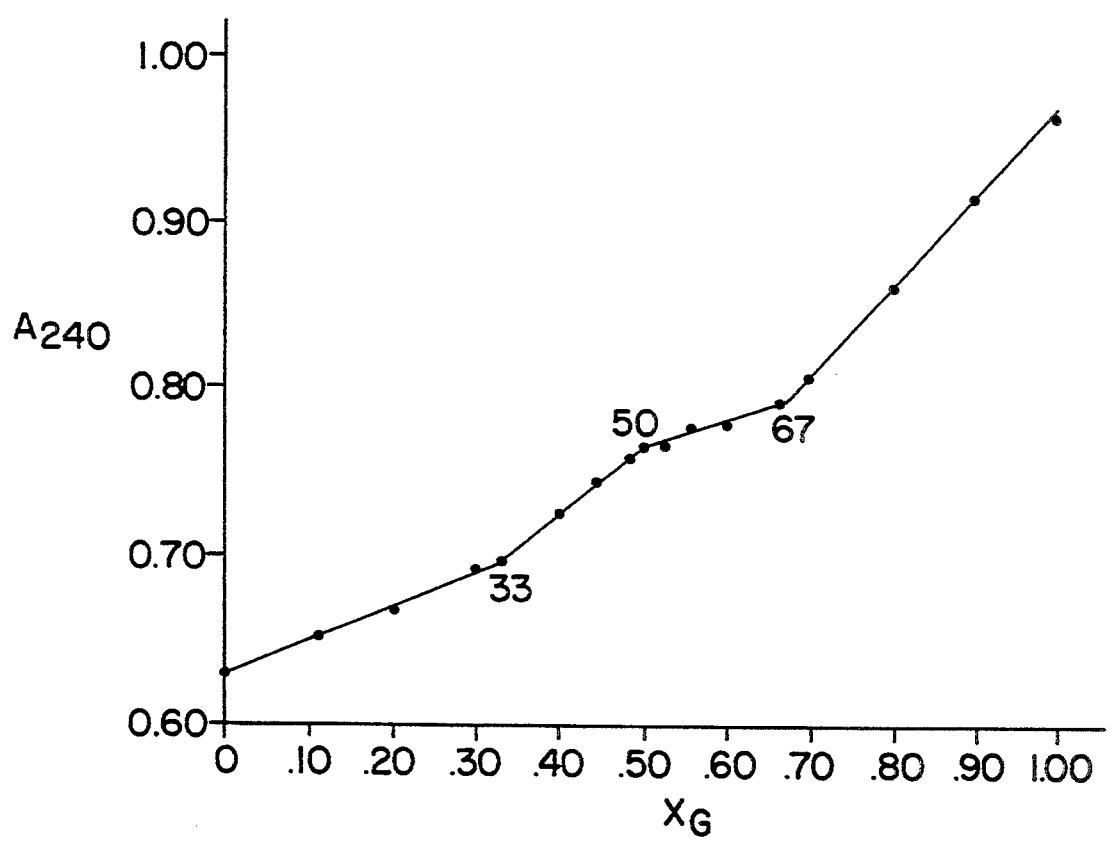
FIG. 11 is a mixing curve plot for the titration of poly($C_{79}$, $I_{21}$) and poly(G).

FIG. 11 shows the mixing curve plot for the titration of poly($C_{79}$, $I_{21}$) and poly(G) at 4° C., pH 7, in the presence of 5 mM $Mg^{+2}$ and 0.15 M $Na^+$. The endpoints corresponding to three stranded complexes fall precisely at $X_G=0.67$. Taking into account the composition of the random copolymer strand participating in each interaction, the complex at $X_G=0.33$ contains 62.4% of its triplets as C·G·C, 16.6% as I·G·C, (16.6% as C·G·I and 4.4% as I·G·I); and the complex at $X_G=0.67$ contains 79% of its triplets as G·G·C (and 21% as G·G·I).

The complex at $X_G=33$ contains triplets with both purine (I) and pyrimidine (C) nucleoside residues in the third strand position; the triplets are incorporated into the triple-stranded structure in exactly the amount predictable from the composition of the random copolymer used for the titration. This demonstrates that there is no bar to having both purine and pyrimidine nucleoside residues in the third strand, which presumably is wound regularly about the core double helix.

EXAMPLE 6

Figure 12:
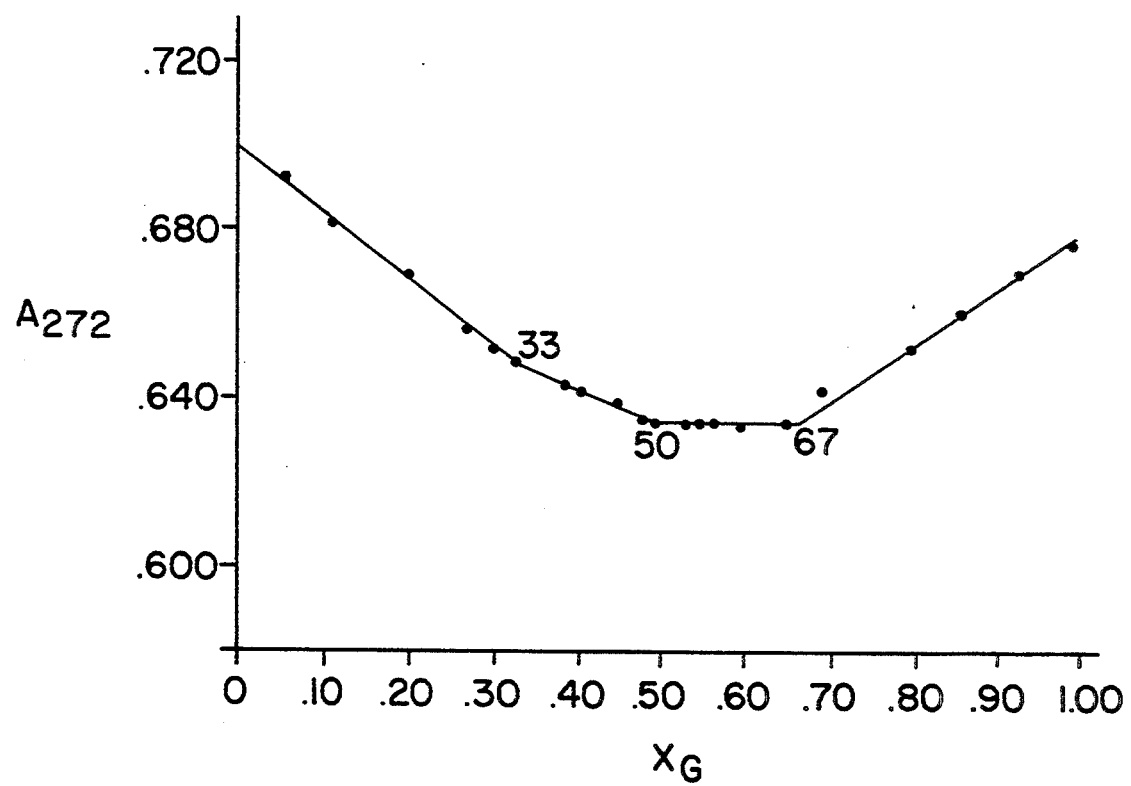
FIG. 12 is a mixing curve plot for the titration of poly($C_{85}$, $G_{15}$) and poly(G).

FIG. 12 shows the mixing curve plot for the titration of poly($C_{85}$, $G_{15}$) and poly(G) at 4° C., pH 7, in the presence of 5 mM $Mg^{+2}$ and 0.15 M $Na^+$. As in Example 5, the endpoints corresponding to three-stranded complexes fall precisely at $X_G=0.33$ and $X_G=0.67$. Taking into account the composition of the random copolymer strand participating in each interaction, the complex at $X_G=0.33$ contains 72.2% of its triplets as C·G·C, 12.8% as G·G·C, (12.8% as C·G·G, and 2.2% as G·G·G); and the complex at $X_G=0.67$ contains 85% of its triplets as G·G·C and (15% as G·G·G).

The complex at $X_G=0.33$ contains triplets with both purine (G) and pyrimidine (C) nucleoside residues in the third strand position. The triplets are incorporated into the triple-stranded structure in exactly the amount predictable from the composition of the random copolymer used for the titration. This provides further evidence that there is no bar to having both purine and pyrimidine nucleoside residues in the third strand.

EXAMPLE 7

The triplets C·G·C, G·G·C, and I·G·C can form at pH 7 in 1 M $Na^+$ or 5 mM $Mg^{+2}$. To prove that third-strand residue protonation is required even at neutral pH for hydrogen bonding to G residues of the double helix, equimolar solutions of poly(G), poly(C), or poly(I) were mixed with poly(G·C) or poly(I·C) at room temperature in unbuffered solvent containing 5 mM $Mg^{+2}$. By scrubbing the solutions with $N_2$ prior to mixing to remove dissolved $CO_2$, and then mixing in an $N_2$ atmosphere, the solutions were brought to neutral pH despite the absence of buffer at the time of mixing. The changes in pH accompanying triple helix formation was then monitored.

If third strand binding does not require protonation, the pH should remain constant during triple helix formation; this was observed in control experiments on mixing unbuffered solutions of poly(U) and poly(A·U). In contrast, formation of poly(C·G·C), poly(I·I·C) and poly(C·I·C) from their respective third-strand and Watson-Crick helix precursors was accompanied by a rise in pH, reflecting proton uptake. Moreover, when the third strand from these three-stranded helices was dissociated upon raising the temperature, the pH dropped back to the value prior to mixing, as the protons abstracted from the solvent upon third-strand binding were shed upon third-strand dissociation.

EXAMPLE 8

The specificity, kinetics, and equilibria of third-strand binding to polypurine sequences of nucleic acid double helices have been further examined in column binding experiments. Various nucleic acid single strands, i.e., third strands, were covalently linked to agarose gels, and the resulting affinity matrices used in columns to test their capacity to bind double stranded nucleic acids of different sequence, as a function of ionic strength, temperature, and time of interaction. These experiments have confirmed the specificity of third-strand binding for polypurine sequences of parallel polarity, based upon the binding code shown previously in the matrix in the Summary of the Invention section.

Use

The fact that the triple-stranded nucleic acids can form under physiological conditions, coupled with the fact that many organisms are known to contain polypurine regions of 10 or more residues in their double-stranded DNA (or RNA) genomes (see below), gives rise to a number of novel uses for triple-stranded nucleic acid formation. These uses fall into several categories: (a) the use of triple-stranded nucleic acids for diagnostic and other identification and gene isolation purposes; (b) the use of triple-stranded nucleic acid formation to control gene expression in cells grown in a fermentation; (c) the use of triple-stranded nucleic acid formation to control expression of bacterial, vital, or eukaryotic genes in a multicellular organism, for example, to treat, in man, animals, or plants, diseases known to be intrinsic to the genetic makeup of the infectious or host organism, or known to be caused by viruses. These uses, which are described in more detail below, make possible novel approaches to commonly-practiced technologies and the development of some new technologies.

Diagnostic Applications

Third-strand binding to target genomic nucleic acid double helices can be used to detect a target DNA sequence, e.g., a DNA sequence characteristic of a particular organism in a sample. The probe is one which can bind to a polypurine region of the double-stranded DNA of the organism and does not hybridize to the other, different polypurine regions that may be present in the sample.

Organisms are known to contain polypurine regions in their double-stranded genomes (generally DNA, but RNA for certain viruses) (see below). Such regions may be identified by a computer search of a genome of an organism, if all or part of the genomic sequence is known; or, for those organisms for which the genomic-sequence is not known, by using the polyinosinate (poly(I)) binding method described below.

Having chosen an appropriate unique polypurine region as the target, a single-stranded nucleic acid probe can be designed, using the third strand binding specifications described above, that will specifically form a triple-stranded nucleic acid segment by binding to the double-stranded target region. Therefore, the probe preferably should not contain an inosine residue, which can-bind to both adenine and guanine.

Single-stranded-nucleic acid probes can be prepared by standard methods. For example, DNA probes can be synthesized by a DNA synthesizer, and RNA probes can be obtained by first making a double-stranded DNA, one strand of which codes for the probe, and then using the SP6 transcription system (for example, Promega Biotech's Riboprobe ™ system) to generate the desired RNA probe. Probes also may be labelled with a variety of labels, for example, with $^{32}P$, by standard techniques.

A third-strand binding assay requires that the target double-stranded nucleic acid in the sample is not denatured. Third-strand binding assays also require that the probes are allowed to interact with the double-stranded nucleic acids in the presence of either 5 mM $Mg^{+2}$ or 1 M $Na^+$, or similar effective charge neutralizing conditions.

Samples containing DNA to be detected are obtained according to standard methods particular to the application. Generally, the cells are lysed, and a deproteinized aqueous extract prepared by standard techniques under conditions that do not denature double helical nucleic acids. In one method, after deproteinizing with phenol or with conventional protease and detergent treatment, the double-stranded DNA-containing extract is brought to 5 mM $Mg^{+2}$. A single-stranded nucleic acid probe (RNA or DNA labelled with a $^{32}P$ or a conventional dye-adduct) with a sequence correspondent to that of the polypurine segment of interest is added to the solution at room temperature, and the solution incubated at least 1 hour at 4° C. to allow probe interaction with correspondent polypurine segments in the target DNA. Since the target DNA is large, and the probe is small, standard gel filtration through a short column of Sephadex G50 (or a molecular sieve with similar exclusion properties) is performed to trap unhybridized labelled probe on the gel, while allowing the larger double-stranded and triple-stranded structures to pass through. The amount of label in the eluent is determined to provide a measure of the triple helix label (the only species labelled) and thereby the quantity of target organism present in the original sample.

Other types of third-strand binding assays may also be employed. For example, instead of performing the assay in solution, the double-stranded DNA of the sample can be attached covalently to a solid support (e.g., cyanogen bromide-activated sepharose on a filter) by following known procedures, and the probe applied to the attached DNA under the appropriate conditions (e.g., pH 7, 5 mM $Mg^{+2}$, 25° C.) to allow binding of probes to target sequences. The amount of label bound to the support, following standard washing, is a measure of the amount of target organism in the original sample. Alternatively, sample DNA need not be isolated; the assay can be performed by immobilizing cells from the sample on a solid support and lysing the cells so as not to denature cellular DNA and under standard conditions where the double-strand DNA remains immobilized on the support.

Control of Gene Expression

Since triple-stranded nucleic acids are stable under physiological conditions (cells generally contain the equivalent of 5 mM divalent cation and 0.15 M $Na^+$), and because polypurine segments are widely distributed in genomic sequences (see below), gene expression may be controlled, using triple strands, at the level of transcription. In order for a genomic double-stranded DNA region to be expressed (i.e., to be functionally active), it must be accessible to transcription by RNA polymerase, which requires some sort of transitory unwinding of the DNA double helix. Binding of a third strand to a double-stranded region (to form a stable triple helix segment) is a deterrent to such unwinding of the double helix (and hence to transcription), since the third strand is wound around the genomic double helix. Accordingly, a gene containing a polypurine region within its coding sequence (including intron sequences) or within or near a promoter (or enhancer element) is effectively inactivated as a result of the binding of a third strand; either transcription will be prevented, or it will be interrupted.

Gene Control in Fermentations

Cells are often fermented in commercial manufacturing processes to produce substances such as drugs, antibiotics, and chemicals. Production of the desired substance is often controlled by the activity of one or just a few genes; this can be the case for cells which naturally produce the desired substance and cells transformed with heterologous DNA molecules encoding a protein not normally synthesized by the cell. In many instances, it is desirable to control gene expression in some way, for example, by repressing expression of a gene encoding a desired protein during the growth phase of the fermentation and inducing expression at the end of growth phase, so that product synthesis is delayed until the cells have reached a desired cell mass. This makes for greater metabolic efficiency in producing first the desired cell mass, and later the desired product; moreover, overproduction of sometimes toxic or unwanted products can be avoided. In addition, repression of a gene during growth avoids plasmid instability due to uncontrolled transcription from a cloned gene. Common means of controlling heterologous gene expression include the use of promoters (e.g., the "tac" promoter, DeBoer, U.S. Pat. No. 4,551,433) or DNA rearrangements (e.g., Backman et al., 1984, Bio/Technology 2:1045–49), which are inducible by a change in growth conditions such as the addition of an inducing chemical or a temperature shift.

Third-strand binding can provide another means to control expression of endogenous or heterologous genes in a fermentation. To control expression of an endogenous gene, there must be an appropriate naturally-occurring polypurine region within or near the gene or its promoter, most preferably within its promoter. To control expression of a heterologous gene (generally introduced into a cell in a recombinant DNA vector), a naturally-occurring polypurine region is not necessary, since a synthetic polypurine fragment may be inserted at a desired location, such as adjacent to or within the promoter, during construction of a vector, using standard recombinant DNA techniques. In either case, the desired gene can be inactivated at the time of choice by the introduction into the cell of an appropriate single-stranded nucleic acid that forms a triple-helix by binding to the target polypurine region.

There are a variety of suitable ways to introduce third-strand nucleic acids into a cell. For example, if the nucleic acid is RNA, it can be synthesized by inducible transcription from the standard SP6 plasmid system where the plasmid has been transformed into the cells. Alternatively, RNA or DNA single strands can be packaged into liposomes, which can be introduced into the fermentation broth at the desired time and taken up by the cells. The amount introduced need not be more than a few ng (D. A. Melton, 82 PNAS 144 (1985)).

Genes can also be activated at a chosen time by inactivating a gene that blocks expression of the desired gene, e.g., a gene encoding a repressor protein, which is capable of binding to a DNA region to block transcription (e.g., the lambda repressor protein).

Gene Control in Multicellular Organisms

Third-strand binding may also be useful in the control of gene expression in multicellular organisms, particularly for the treatment of human and animal diseases known to be linked to the expression of one or more host genes, and also in the control of replication of viruses that infect cells of higher organisms. In this application, the formation of a triple-stranded nucleic acid between double-strand genomic DNA and an introduced third strand can be used to block gene expression, by the means described above, in specific cells of a multicellular organism.

Several diseases are suspected of being caused by overexpression of certain gene products. For example, bladder cancer is known to be caused by overexpression of certain proteins. In addition, vital diseases are caused when viruses subvert the genetic machinery of an organism's cells, causing vital genes to be expressed in the host's cells, thereby creating new infectious virus particles.

Third-strand binding can be used to treat such genetic diseases by blockage of gene expression analogously to the procedures described above. A suitable naturally-occurring unique polypurine region within the gene or near its control regions is located either through a search of the known sequence or by the use of the poly(I) method described below and an appropriate single-stranded nucleic acid designed to bind specifically to the polypurine region as described above.

As is the case for fermentative gene control, the third strand must be introduced into the cells affected by the disease. In general this is done inside a living organism, although the method might be applicable to treatment of cells which have been removed from the organism, to be returned after treatment (e.g., bone marrow cells and blood cells). A suitable delivery system is chosen to introduce the third strand: possibilities include liposomes and retrovital vectors (Gilboa et al., 83 PNAS 3194 (1986)), which are capable of introducing genes that code for intact single-stranded nucleic acids inside cells.

Identification of Polypurine Regions

Methods of finding polypurine regions in double-stranded nucleic acids include inspecting the published or experimentally-determined base sequences of genes and even whole genomes, and use of $P^{32}$-labelled-short polyinosinate strands to screen double-stranded nucleic acids of unknown base sequence for polypurine segments.

The complete base sequences of three genomes (Bacteriophage λ, which has 48,502 base pairs; Simian virus 40 (SV40), which has 5,243 base pairs; and Adenovirus type 2, which has 35,937 base pairs), and part of the sequences (available in GENBANK) of E. coli and humans, were examined for polypurine regions. Table 1 presents some of the results of these searches. For E. coli, 111 genes were examined and 225 polypurine segments of 10 residues or more were found, an average of approximately 2 polypurine segments per gene. The 50 genes in the Bacteriophage λ genome contained 52 polypurine segments of 10 residues or more, an average of approximately 1 polypurine segment per gene. The 6 genes of SV40 contained 15 polypurine segments of 10 or more residues, an average of 2.5 segments per gene. The 50 genes of Adenovirus type 2 contained 50 polypurine segments of 10 or more residues, an average of one polypurine segment per gene. Finally, the 459 human genes examined had a total of 2,087 polypurine segments, an average of about 4.5 segments per gene.

TABLE 1

| | # of genes examined | # of all-purine segments found | segments/gene |
|---|---|---|---|
| E. coli | 111 | 225 | 2 |
| Bacteriophage λ | 50 | 52 | 1 |
| SV40 | 6 | 15 | 2.5 |
| Adenovirus type 2 | 50 | 50 | 1 |
| Human | 459 | 2087 | 4.5 |

Polypurine segments can be identified in organisms where DNA base sequences are unknown by utilizing the third-strand binding properties of poly(I). Accordingly, using standard techniques, double-stranded DNA is isolated from the organisms and digested with standard, appropriate restriction enzymes. Alternatively, polypurine segments may be identified within or near genes that have been cloned by digesting the cloned DNA of the gene with restriction enzymes by standard techniques. The digested DNA is passed through a sepharose column to which poly(I) strands are covalently bound by standard techniques. Inosine residues bind to both adenosine and guanosine residues and therefore recognize any polypurine segment on the double-stranded digest fragments of DNA. By running the column at 22° C., pH 7 in the presence of 5 mM $Mg^{+2}$, those restriction fragments that contain polypurine segments bind to the poly(I) strands, while fragments that do not contain polypurine segments pass through the column. The temperature of the column then is raised and/or the column is rinsed with aqueous solvent containing reduced cation concentrations to cause polypurine segments to dissociate from the poly(I) strands and pass through the column. These eluted fragments are fractionated by standard agrose gel electrophoresis techniques under non-denaturing conditions suitable for third strand binding. The polypurine-containing bands are then located by radioautography after being allowed to interact with $^{32}$P-labelled poly(I) on the gel matrix, and then eluted and sequenced. With a knowledge of the polypurine segment sequences, appropriate RNA or DNA third strands are synthesized by standard methods. Alternatively, cellular RNA can be searched by standard methods for the presence of natural third strands corresponding to those polypurine targets.

Other Embodiments

Other embodiments are within the following claims. For example, organic polyamines such as spermine and spermidine may be used as the site bound cation to provide the appropriate ionic condition for third strand binding to occur. Moreover, the structures of the base residues adenine, cytosine, guanine, thymine, uracil, and hypoxanthine may be modified slightly (to form base analogues) so long as the modification does not preclude the hydrogen bonding schemes required by the respective base for specific third-strand binding. In fact, the words adenine, cytosine, guanine, thymine, uracil, and hypoxanthine should be understood to encompass such slight structural modifications in the respective parent bases. Otherwise long purine segments that contain an occasional pyrimidine should also be capable of third strana binding; accordingly, the term polypurine segment should be understood to include those segments in which at least 90% of the bases are purines, and the interrupting pyrimidines in the sequence are singles (neighbored by purines on both the 5' and 3' sides). The second nucleic acid strand may contain an occasional nucleic acid residue (e.g., one per thousand) that is not complementary in a Watson-Crick manner to its hydrogen bonding partner in the polypurine segment and still be capable of hydrogen bonding with the polypurine segment; accordingly the second strand should be understood to include such strands.

I claim:

1. A method of forming a triple-stranded nucleic acid comprising the steps of:
   providing a first nucleic acid strand comprising a region of at least ten adjacent purine nucleoside residues;
   providing a second nucleic acid strand which is hydrogen bonded in a Watson-Crick manner to said region of adjacent purine nucleoside residues;
   providing a third nucleic acid strand comprising at least one purine residue and at least one pyrimidine nucleoside residue; and
   contacting said first and second strands with said third strand at a pH between 6 and 8 so as to allow formation of hydrogen bonds between the nucleoside residues of said third strand and said region of adjacent purine nucleoside residues of said first strand so as to form said triple-stranded nucleic acid wherein adenosine in said first strand is hydrogen bonded to one of adenosine, uridine, thymidine and inosine in said third strand and guanosine in said first strand is hydrogen bonded to one of guanosine, cytidine and inosine in said third strand.

2. The method of claim 1, wherein said first and second strands comprise RNA.

3. The method of claim 1, wherein said third strand comprises RNA.

4. The method of claim 1, wherein said first and second strands comprise DNA.

5. The method of claim 1, wherein said third strand comprises DNA.

6. The method of claim 4, wherein said third strand comprises RNA.

7. The method of claim 1, wherein said first strand and said third strand comprise heteropolynucleotides.

8. The method of claim 1, wherein said region of adjacent purine nucleoside residues is at least 90% purine residues, and any interrupting pyrimidines are single pyrimidines.

9. The method of claim 1, wherein at least one nucleoside residue in the third strand is substituted with a base analog.

10. A method of forming a triple-stranded nucleic acid comprising the steps of:
    providing a first nucleic acid strand comprising a region of at least ten adjacent purine nucleoside residues;
    providing a second nucleic acid strand which is hydrogen bonded in a Watson-Crick manner to said region of adjacent purine nucleoside residues;
    providing a third nucleic acid strand comprising at least one adenosine residue; and
    contacting said first and second strands with said third strand at a pH between 6 and 8 so as to allow formation of hydrogen bonds between the nucleoside residues of said third strand and said region of adjacent purine nucleoside residues of said first strand so as to form said triple-stranded nucleic acid wherein said third strand contains at least one adenosine which is hydrogen bonded to an adenosine in said adjacent purine nucleoside residues of said first nucleic acid strand.

11. The method of claim 10, wherein said first and second strands comprise RNA.

12. The method of claim 10, wherein said third strand comprises RNA.

13. The method of claim 10, wherein said first and second strands comprise DNA.

14. The method of claim 10, wherein said third strand comprises DNA.

15. The method of claim 13, wherein said third strand comprises RNA.

16. The method of claim 10, wherein said first strand and said third strand comprise heteropolynucleotides.

17. The method of claim 10, wherein said region of adjacent purine nucleoside residues is at least 90% purine residues, and any interrupting pyrimidines are single pyrimidines.

18. The method of claim 10, wherein at least one nucleoside residue in the third strand is substituted with a base analog.

* * * * *

UNITED STATES PATENT AND TRADEMARK OFFICE
CERTIFICATE OF CORRECTION

PATENT NO. : 5,422,251
DATED : June 6, 1995
INVENTOR(S) : Jacques R. Fresco

It is certified that error appears in the above-indentified patent and that said Letters Patent is hereby corrected as shown below:

Column 1, line 16, "polyridylate" should read --polyuridylate--.

Column 2, line 65, "protonetion" should read --protonation--.

Column 8, line 30, "copolynucleotiaes" should read --copolynucleotides--.

Column 9, line 38, "33" should read --0.33--.

Column 13, lines 46 and 48, each occurrence of "vital" should read --viral--.

Column 15, line 29, "strana" should read --strand--.

Signed and Sealed this

Nineteenth Day of December, 1995

*Attest:*

BRUCE LEHMAN

*Attesting Officer*     *Commissioner of Patents and Trademarks*